(12) United States Patent
Bertrand

(10) Patent No.: US 7,398,146 B2
(45) Date of Patent: Jul. 8, 2008

(54) MEASUREMENT OF THE MAXIMUM ADHESION COEFFICIENT BY MEASURING STRESS IN A BEAD OF A TIRE

(75) Inventor: David Bertrand, Chamalieres (FR)

(73) Assignee: Michelin Recherche Et Technique S.A. (CH)

( * ) Notice: Subject to any disclaimer, the term of this patent is extended or adjusted under 35 U.S.C. 154(b) by 380 days.

(21) Appl. No.: 11/015,353

(22) Filed: Dec. 17, 2004

(65) Prior Publication Data

US 2005/0159874 A1    Jul. 21, 2005

Related U.S. Application Data

(63) Continuation of application No. PCT/EP03/06510, filed on Jun. 20, 2003.

(30) Foreign Application Priority Data

Jun. 24, 2002    (FR) .................... 02 07809

(51) Int. Cl.
G01M 17/02    (2006.01)
(52) U.S. Cl. .................... 701/80; 73/146
(58) Field of Classification Search .......... 701/80, 701/73–74, 82; 303/149, 150; 73/146
See application file for complete search history.

(56) References Cited

U.S. PATENT DOCUMENTS

| 3,852,993 | A | 12/1974 | Dobychin et al. ........... 73/12.06 |
| 4,715,662 | A | 12/1987 | van Zanten et al. ......... 303/150 |
| 4,862,368 | A | 8/1989 | Kost et al. .................... 701/74 |
| 5,864,056 | A * | 1/1999 | Bell et al. ..................... 73/146 |
| 5,892,139 | A | 4/1999 | Miyazaki ......................... 73/9 |
| 5,964,265 | A | 10/1999 | Becherer ................. 152/152.1 |
| 6,266,600 | B1 | 7/2001 | Miyazaki ..................... 701/71 |
| 6,338,270 | B1 | 1/2002 | Mancosu et al. .............. 73/146 |
| 6,339,956 | B1 | 1/2002 | Huinink et al. |
| 6,429,788 | B2 | 8/2002 | Matsumoto et al. |
| 6,430,993 | B1 | 8/2002 | Seta ............................. 73/146 |
| 6,564,625 | B1 | 5/2003 | Ishiyama ..................... 73/146 |
| 6,725,168 | B2 * | 4/2004 | Shiraishi et al. ............... 702/81 |
| 6,962,075 | B2 | 11/2005 | Bertrand |
| 7,069,135 | B2 | 6/2006 | Bertrand |
| 7,099,765 | B2 | 8/2006 | Bertrand |
| 2002/0157746 | A1 | 10/2002 | Merino-Lopez et al. .. 152/209.5 |
| 2002/0166373 | A1 | 11/2002 | Mancosu et al. .............. 73/146 |
| 2003/0182045 | A1 | 9/2003 | Miyazaki ..................... 701/70 |
| 2004/0158414 | A1 | 8/2004 | Bertrand |

FOREIGN PATENT DOCUMENTS

DE    44 35 448 A    4/1995

(Continued)

*Primary Examiner*—Dalena Tran
(74) *Attorney, Agent, or Firm*—Fitzpatrick, Cella, Harper & Scinto

(57) ABSTRACT

A method of determining a friction coefficient $\mu$ in a contact area of a tire on a road. Fixed points are selected that lie at different azimuths along a circumference of at least one bead of the tire. A shear stress value is measured at each of the fixed points while the tire is rolling on the road. The measured shear stress values are processed to determine the friction coefficient $\mu$.

11 Claims, 12 Drawing Sheets

FOREIGN PATENT DOCUMENTS

| | | |
|---|---|---|
| EP | 1 095 794 A | 5/2001 |
| JP | A1-2000-203217 | 7/2000 |
| JP | A1-2002-004931 | 1/2002 |
| WO | WO 01/09278 | 2/2001 |
| WO | WO 01 36241 A | 5/2001 |

* cited by examiner

Shear stresses at point A

Stresses (daN/mm²)

Azimuth (Deg)

Shear stresses at point B

Stresses (daN/mm²)

Azimuth (Deg)

Shear stresses at point A

Shear stresses at point B

Shear stresses at point A

Shear stresses at point B

Figure 7
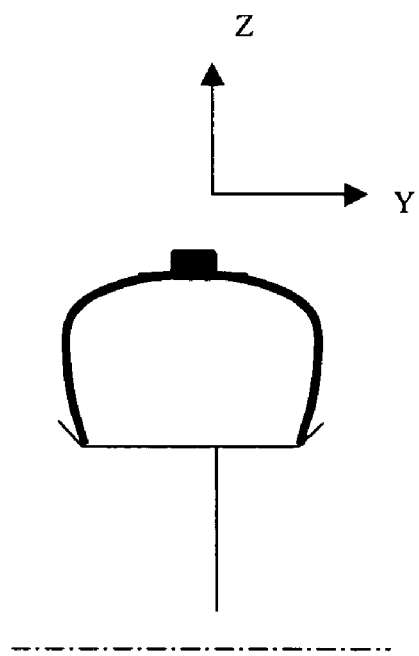
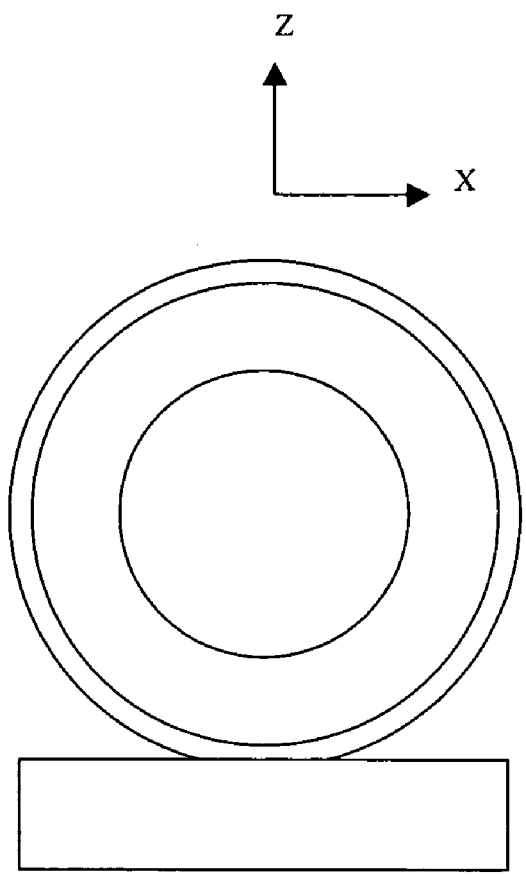
Figure 8

MEASUREMENT OF THE MAXIMUM ADHESION COEFFICIENT BY MEASURING STRESS IN A BEAD OF A TIRE

CROSS-REFERENCE TO RELATED APPLICATIONS

This application is a continuation of International Application No. PCT/EP03/006510, filed Jun. 20, 2003, which is incorporated herein by reference in its entirety.

BACKGROUND OF THE INVENTION

1. Field of the Invention

The present invention relates to the evaluation of the grip of a vehicle on a road. It relates more particularly to the determination of friction characteristics between the road and a vehicle wheel fitted with an elastic tire, such as an inflated pneumatic tire or a non-pneumatic elastic tire, which rolls on the road.

The present invention also relates to the various electronic assistance devices used, for example, for antilock control of the brakes of a vehicle or antiskid control of the drive wheels, control of the trajectory of a vehicle or other forms of control or monitoring, such as the tire pressures. It is known that such devices reconstruct the friction coefficient ($\mu$) of the tires on the road by calculation, without having carried out any measurement either of the friction coefficient or of the forces developed in the contact of the tires with the ground. Even though these devices provide significant assistance and extra safety, their operation would benefit greatly from the use of a measured value, or a value estimated from real measurements carried out on the tire during operation.

For this reason, it is an object of the present invention to provide a way of evaluating the grip of a vehicle on a road, and more precisely of its wheels or tires or elastic tires, these terms being regarded as equivalent in the context of the present invention. It relates more particularly to the determination of friction characteristics between the road and a vehicle wheel fitted with an elastic tire, such as an inflated tire or a non-pneumatic elastic tire, which rolls on the road.

2. Related Art

The various electronic assistance devices mentioned above would therefore usefully benefit from "real-time" indications of the grip conditions liable to affect the handling of a vehicle, especially when it undergoes an acceleration due to a driving force or a braking force, or due to a change of direction of movement. The invention aims to provide a method of achieving this efficiently.

In what follows, "maximum friction potential" refers to the ratio between the maximum tangential force (transverse or longitudinal, or both combined) and the normal force which the wheel can experience. In the text, this is also denoted by the term "maximum friction coefficient", or the letter $\mu$.

"Overall forces" refers to the three components of forces Fx, Fy and Fz applied to the center of the wheel, and the self-alignment torque N about the axis Z.

With a view to estimating the maximum friction potential, it is proposed that the tread of a tire, or certain specially adapted elements of the tread, be fitted with sensors intended to measure or estimate the forces generated locally, in particular under slip conditions. Although highly promising, these approaches nevertheless involve certain intrinsic difficulties. Indeed, it is difficult to ensure correct operation of a sensor in this region of a tire, in particular when there is a wear of the tread, throughout the life of the tire. Furthermore, the estimates provided by these sensors are highly local and sensitive to the surface condition of the road.

Moreover, since the intention is actually to estimate the maximum friction potential of the wheel, this still remains to be determined from the measured local potential.

SUMMARY OF THE INVENTION

The invention described in detail here differs from these local approaches. It proposes to use a measurement of the stresses generated by the overall deformations of the tire so as to obtain information about the maximum friction potential of the wheel on the ground. Specifically, when the tire is subjected to a constraint, the point of application of the forces being applied in the contact area depends, inter alia, on the maximum friction coefficient, because, as soon as a part of the contact area of the wheel on the road slips, its contribution to the tangential forces is saturated at a level which depends on the friction coefficient. The deformations of the tire are themselves sensitive to the movement of this point of application. In particular, these deformations create stresses in the bead. These stresses, which are sensitive to the applied forces, are also sensitive to the movement of the point of application of the forces in the contact area.

The proposed method uses measurements of the stresses in the bead or beads at certain azimuths of the tire in order to allow estimation of the maximum friction coefficient.

In order to obtain a good estimate of $\mu$, the method requires that there be a slip region in the contact area, created either by a special design of the tire or by a sufficient level of constraint applied to the tire. In order to obtain reliable information even when there is little slipping, the invention proposes that a percentage potential be estimated in addition to the maximum friction potential. The reason is that this quantity has the advantage of being easier to estimate as an absolute value, even for small constraints.

The method according to the invention for determining the friction coefficient $\mu$ in the contact area of a tire on a road includes the following steps:

(a) selecting a plurality of fixed points in space (that is to say ones that are fixed in the reference frame associated with the vehicle), which lie at different azimuths along the circumference in at least one bead of the tire;

(b) carrying out a corresponding number of measurements of stress variation at these fixed points when the tire is rolling on the road; and (c) processing the measurement signals so as to extract the friction coefficient $\mu$ from them.

Advantageously, the friction coefficient $\mu$ is derived from at least 5 measurements of stresses carried out in at least one bead of the tire, at 5 fixed points in space (that is to say ones that are fixed in the reference frame associated with the vehicle) which lie at different azimuths along the circumference.

The method of the invention is based on recognition of the fact that the forces acting between the tread of the tire and the road cause a deformation of the sidewalls of the tires, which give rise to the appearance of substantial and reproducible stresses in the bead. These stresses, if it is possible to measure them individually during rotation of the tire in real time, can make it possible to ascertain at each instant the direction and magnitude of the forces acting on the tire, as well as the sign and the magnitude of the self-alignment torque exerted by the tire and the friction coefficient of the tire on the road.

According to one particular but interesting aspect, the invention proposes to estimate the shear stress in the circumferential direction.

BRIEF DESCRIPTION OF THE DRAWINGS

The rest of the description explains the invention in more detail with the aid of the appended figures, in which:

FIG. 7 is a front schematic view of a tire.

FIG. 8 is a side schematic view of a tire.

DETAILED DESCRIPTION OF THE PREFERRED EMBODIMENTS

The method described here relies on the fact that each force applied to the tire in the contact area causes a deformation of the sidewalls of the tire, which entails a shear stress in the bead. The case of an inflated tire fitted on its wheel will be considered, in the first bead of which the shear stress is measured in the circumferential direction. In the absence of any forces being applied to the tire, the measured stress is constant as a function of the angle of rotation of the tire-wheel assembly.

The azimuth θ will be defined as the angle at which the shear stress in the bead is being analyzed. The origin of the azimuth is taken on the opposite side from the center of the contact area. The center of the contact area therefore has the azimuth 180°.

Figure 1:
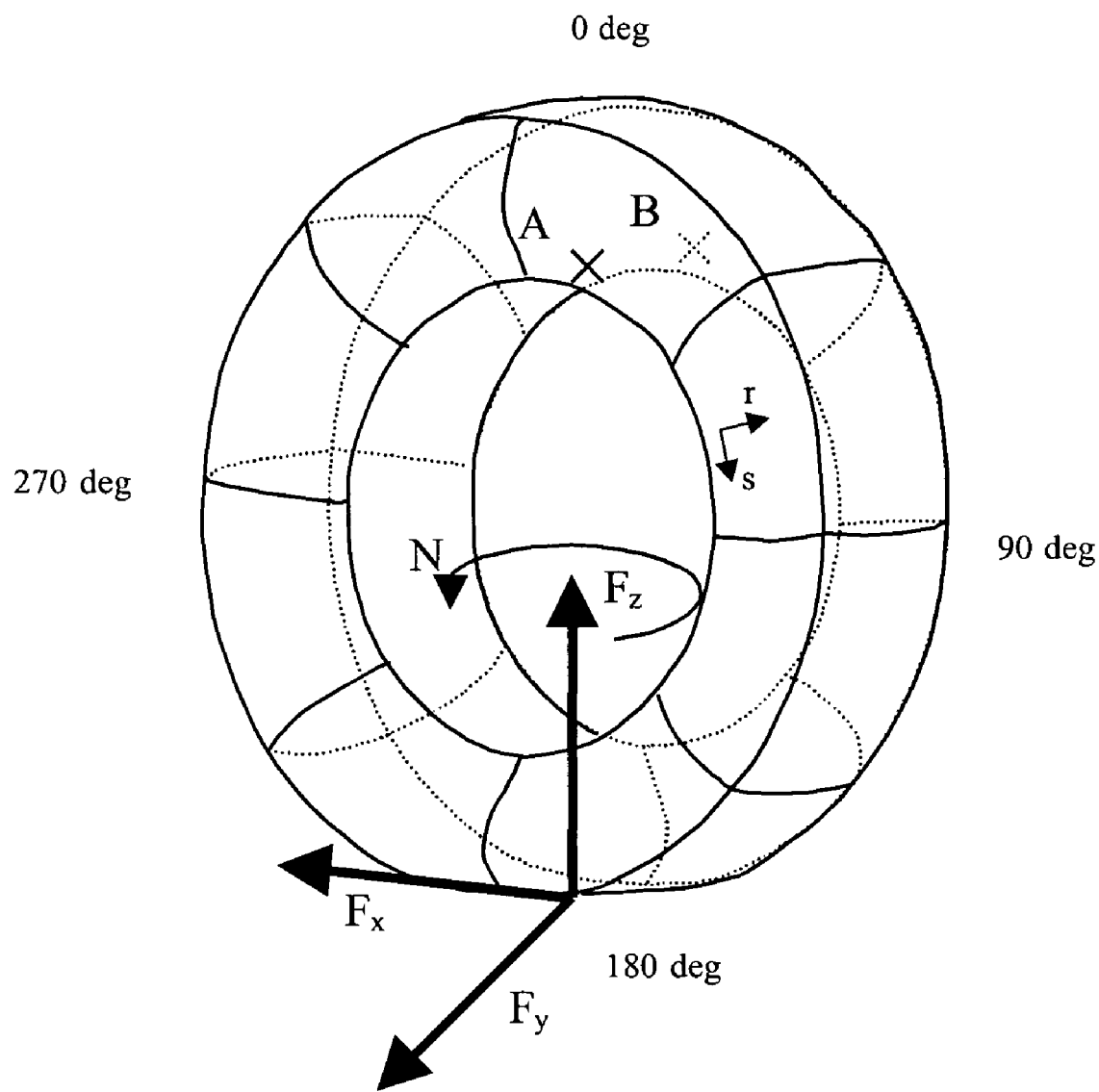
FIG. 1 is a perspective view of a tire in which conventions useful for understanding the invention are defined.
Figure 2A:
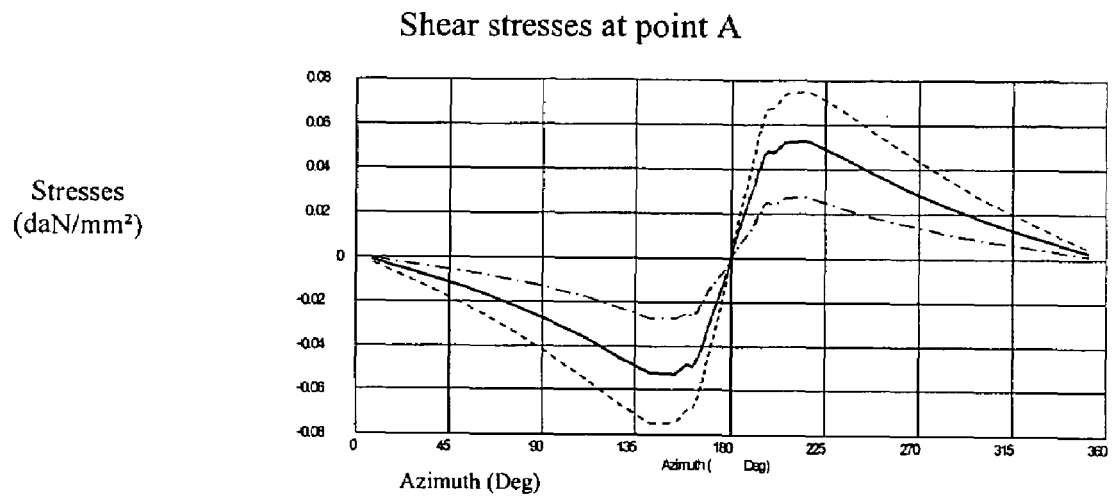
FIGS. 2a and 2b show the effect of the vertical component Fz on the stress $\sigma_{rs}$ in which: the solid curve corresponds to a vertical load of 400 daN; the dotted curve corresponds to a vertical load of 500 daN; and the dotted and dashed curve corresponds to a vertical load of 300 daN.
Figure 2B:
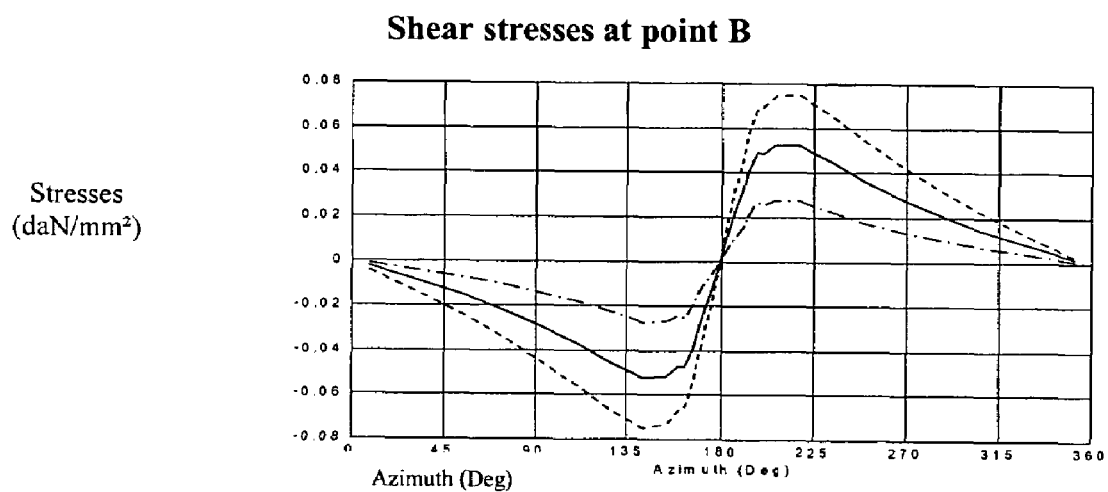

When the tire is subjected to forces, the following effects are observed for each of the components of the forces:

(a) The vertical component (denoted by Fz) presses the tire onto the ground. By creating a contact area, it leads to displacement of the wheel with respect to the center of the tire belt. This results in deradialization, which entails a variation of the shear stresses in the bead. The latter is sheared in one direction before the contact area and in the other direction after the contact area, as indicated by FIGS. 2a and 2b.

Figure 3A:
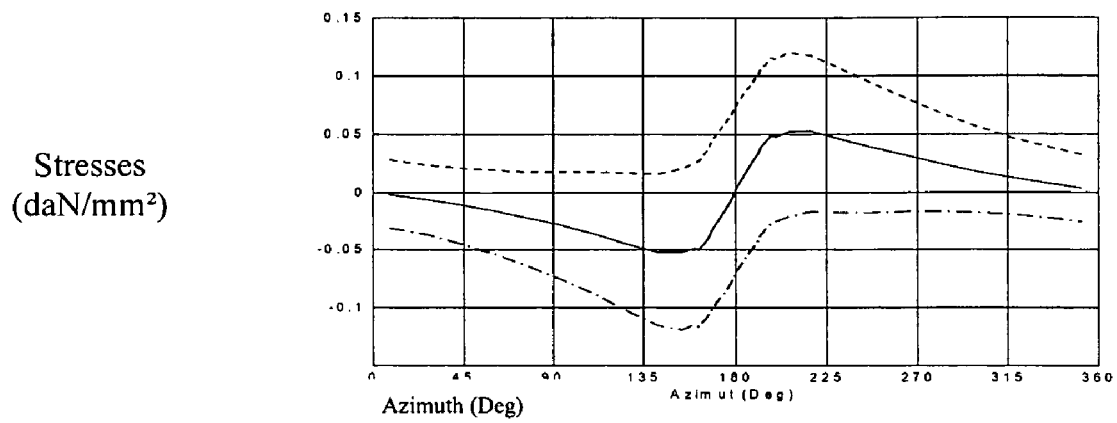
FIGS. 3a and 3b show the effect of the component Fx on the stress $\sigma_{rs}$ in which: the solid curve corresponds to a vertical load of 400 daN and no force Fx; the dotted curve corresponds to a vertical load of 400 daN and a force of Fx–400 daN (braking); and the dotted and dashed curve corresponds to a vertical load of 400 daN and a force Fx of 400 daN (driving).
Figure 3B:
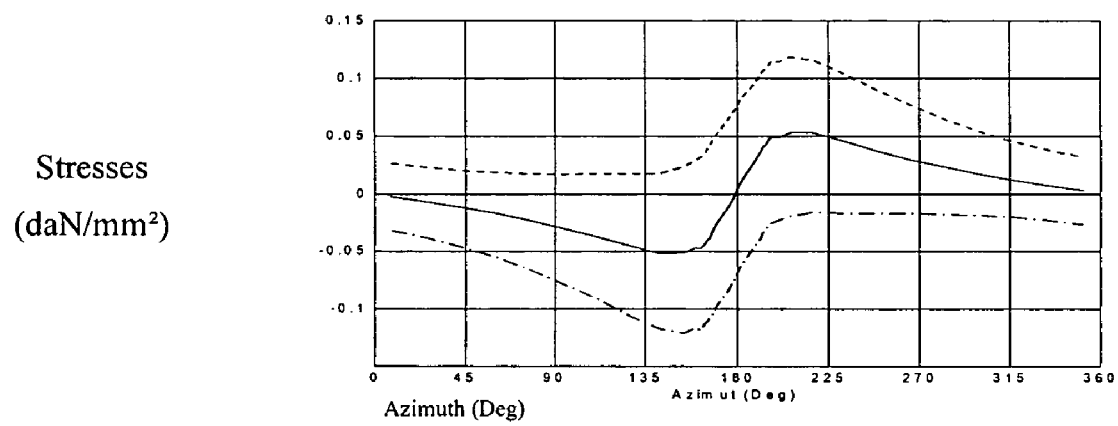

(b) The horizontal component in the rolling direction (denoted by Fx) causes a slight rotation of the wheel with respect to the tire belt. This results in a substantially uniform azimuthal shear in one or other direction. The direction of the additional shear indicates the driving or braking nature of the applied force. FIGS. 3a and 3b show the effect of the component Fx.

Figure 4A:
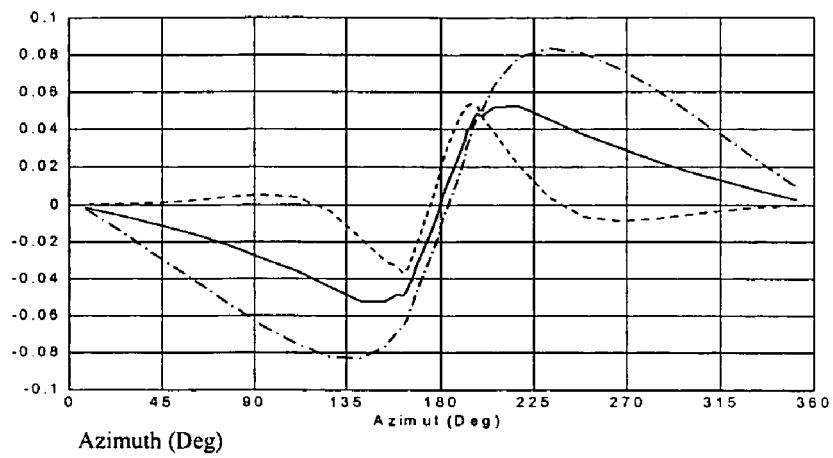
FIGS. 4a and 4b show the effect of the component Fy on the stress $\sigma_{rs}$ in which: the solid curve corresponds to a vertical load of 400 daN with no force Fy; the dotted curve corresponds to a vertical load of 400 daN with a force Fy of 280 daN; and the dotted and dashed curve corresponds to a vertical load of 400 daN with a force Fy of –280 daN.
Figure 4B:
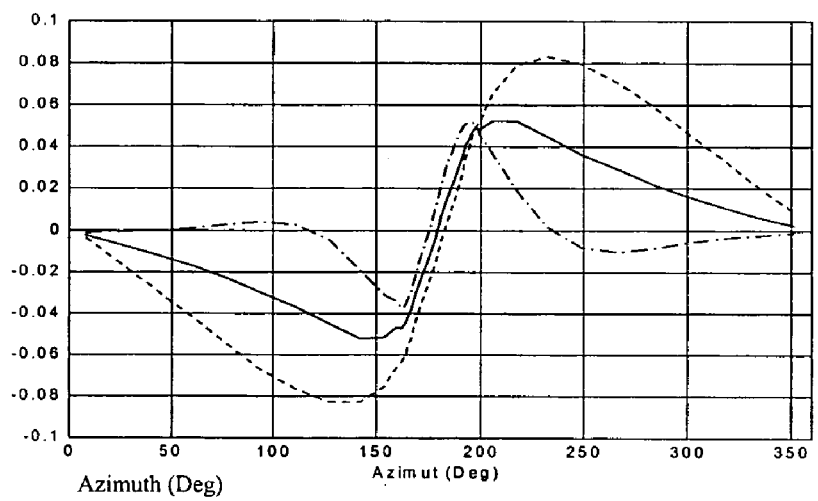

(c) The horizontal component in the transverse direction (denoted by Fy) principally causes differentiation between the two beads. In the case of a constraint due to Fy, one of the sidewalls principally experiences extension. Deradialization develops, and this results in a different distribution of the shears in the bead. The other sidewall experiences contraction and the opposite effect takes place in the bead, as demonstrated by FIGS. 4a and 4b.

The self-alignment torque N (moment about the vertical axis) is not, strictly speaking, a force acting between the tread of the tire and the road. Rather, it is a consequence of the way in which the components Fx, Fy and Fz are applied in the contact area. If the point of application of the resultant, whose components are Fx, Fy and Fz, is not the center of the contact area, this resultant generates a moment about Oz, which is referred to as the self-alignment torque. The existence of this moment principally entails a rotation of the contact area about Oz. The consequence of this effect is to induce a shear in one direction on the first sidewall and in the other direction on the second sidewall, in proximity to the contact area.

When a constraint which mixes components Fx, Fy and Fz is applied, a superposition of the aforementioned effects on the shear stress in the circumferential direction is observed. One of the advantages of the proposed method is that it permits the contributions of each component of the applied constraint to be separated, so as to make it possible to estimate each of these components.

Figure 5:
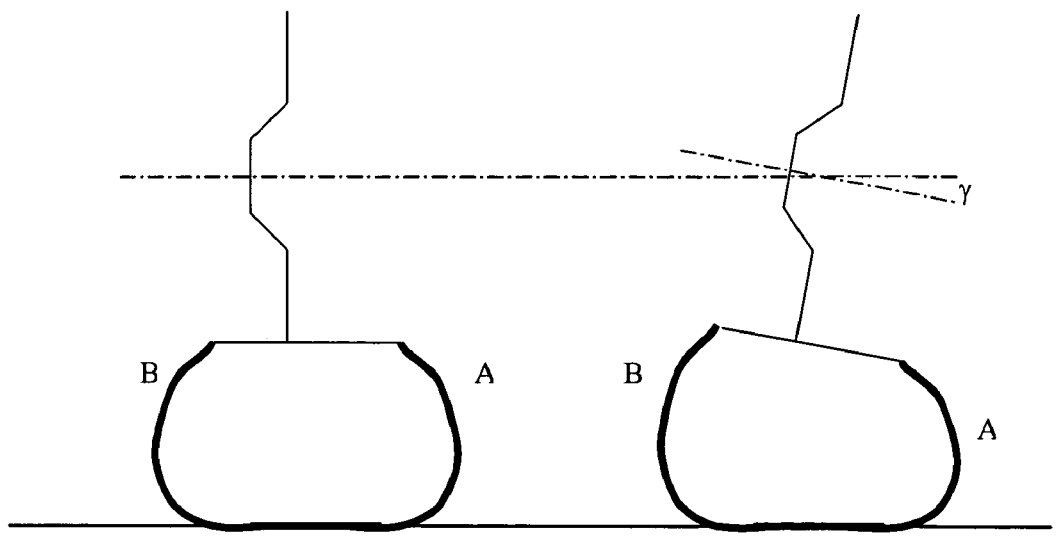
FIG. 5 shows the deformation of the tire when a camber angle is applied.
Figure 6A:
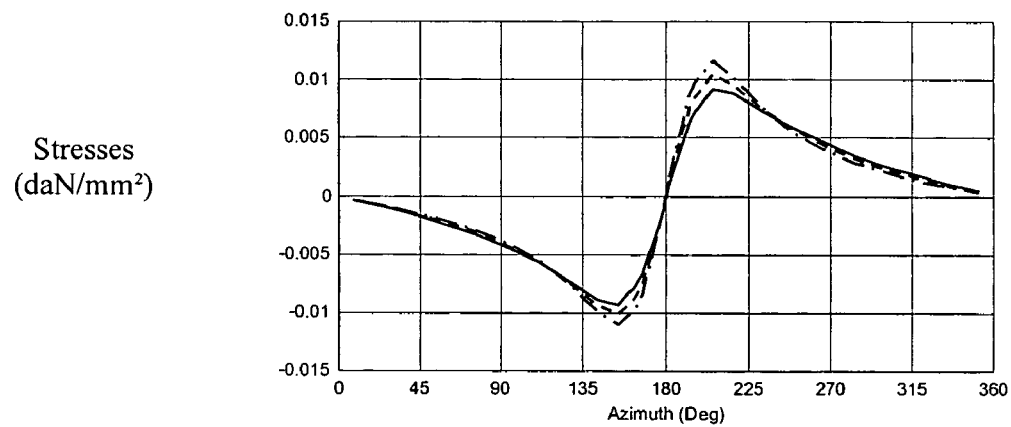
FIGS. 6a and 6b show the effect of the camber on the shear stress signals in which: the solid curve corresponds to a vertical load of 400 daN with no forces Fx and Fy, and to a zero camber angle; the dotted curve corresponds to a vertical load of 400 daN with a camber angle of 2°; and the dotted and dashed curve corresponds to a vertical load of 400 daN with a camber angle of 4°.
Figure 6B:
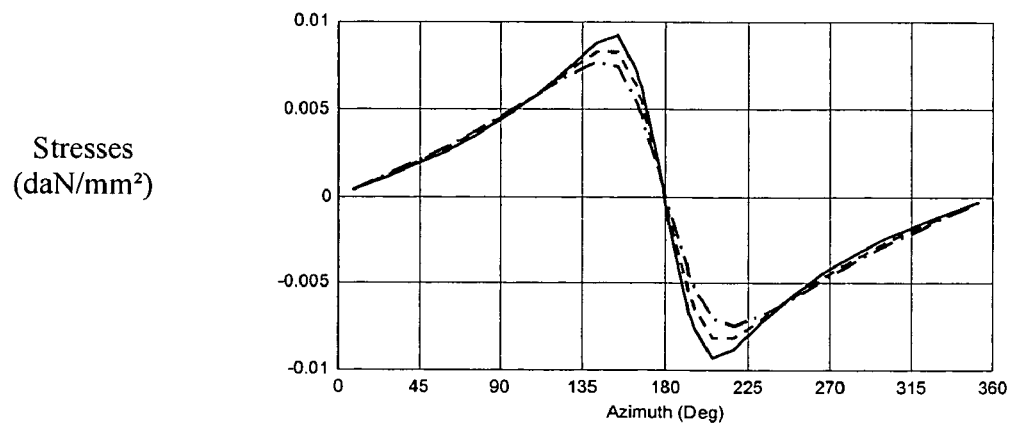

In the event that a camber angle is applied to the tire, the behavior of the two sidewalls, and therefore of the two beads, differs. In other words, it appears as if one sidewall were carrying more load than the other. FIG. 5 illustrates this behavior by comparing a cross section of the part of the tire in the contact area without any camber and with a camber γ. This also results in a slight lateral displacement of the contact area, which entails a thrust in the Y direction. FIGS. 6a and 6b show the change in the circumferential shear stresses in the two beads. On the overloaded bead (points A), the change is similar to that of an increase in the load. On the other bead (points B), a change is seen which is compatible with a decrease in the load being supported. This change in the signals corresponds to a rotation of the contact area about the axis Ox.

The apparent rigidity of a tire originates both from its pneumatic behavior (from its inflation pressure) and from its structural rigidity (rigidity of its architecture). The measured shear stress signals themselves also contain a pneumatic component and a structural component. For example, the shear signals of a tire inflated to 2 bar and loaded with 400 daN along Z are not identical to those delivered by the same tire at 2.5 bar and loaded with 500 daN. This difference corresponds to the structural contribution, and can make it possible to estimate the inflation pressure of the tire.

As inflation pressure varies, the relationships which link the applied forces and the shear signals are quantitatively modified, but without their nature being changed. The method may thus be explained firstly in the case of an inflation pressure which is assumed to be constant, for the sake of simplicity. Likewise, it will be assumed below that the camber is constant and zero, in order to make the explanation clearer, and only the most interesting cases concerning this parameter will be mentioned.

Figure 9:
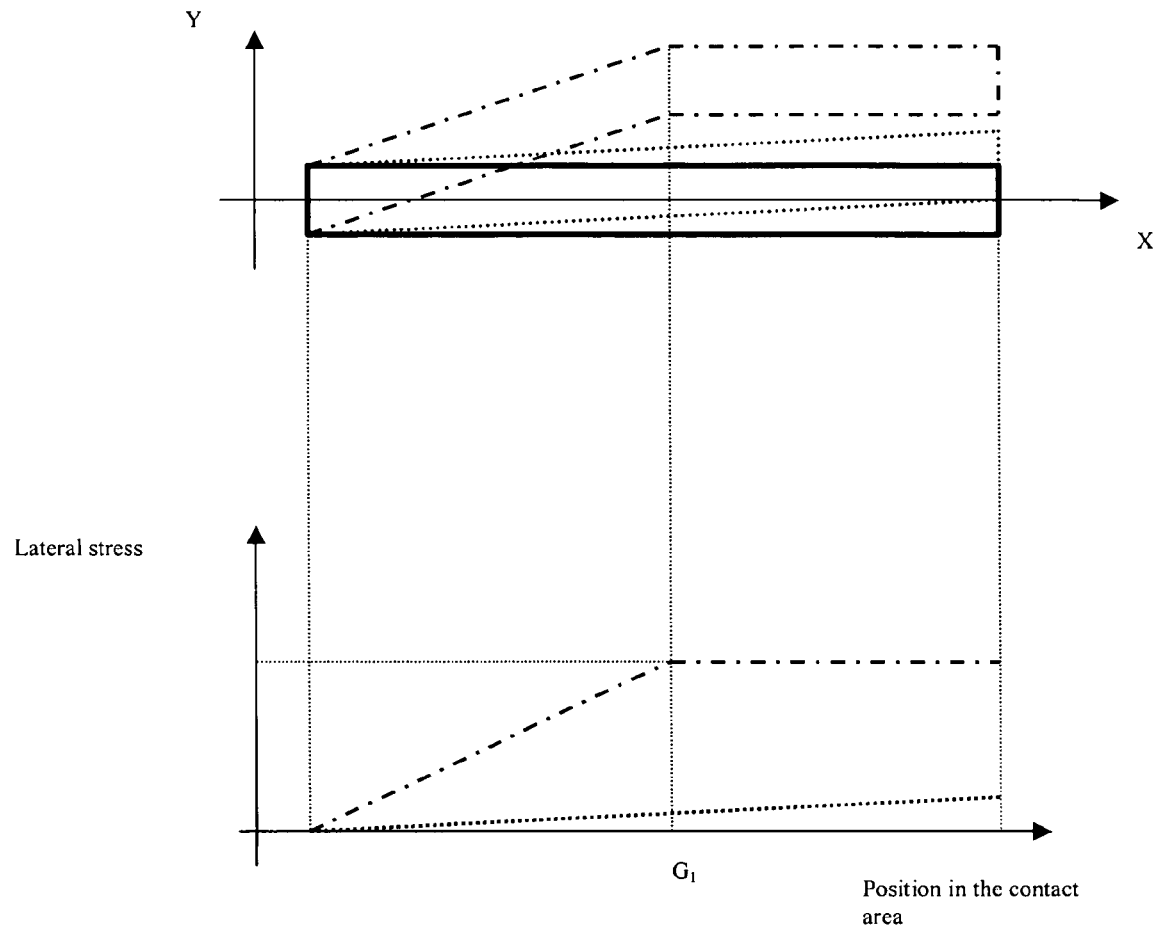
FIG. 9 illustrates the shearing of a rib in the contact area, as well as the associated stresses.

The invention is based on the following observation: a simplified tire provided with a single continuous rib will be considered. FIGS. 7 and 8 represent such a tire. In the region of the contact area, the rib is subjected to a vertical stress which presses it against the ground. This is often referred to as flattening, in the footprint of the tire on the ground. If there is no drift angle applied to the tire, a straight line is formed by reference points defined on the rib (the straight line being aligned with the contact footprint) as the reference points pass through the contact footprint. As the tire rotates, these reference points lie in a plane containing this straight line. If a drift angle is applied to the tire while it is rolling, the plane containing the reference points (when the reference points are sufficiently far from the contact footprint), forms an angle with respect to the contact footprint equal to the drift angle. The solid line in FIG. 9 shows the rib seen from above with no drift, and the dotted line shows the rib with an imposed drift. The more the contact area is pressed in, the more the rib is sheared and the greater is the lateral stress which is applied. If the drift angle is sufficient, there is a point $G_1$ in the contact area where the ratio of this lateral stress to the vertical stress becomes greater than the maximum friction potential $\mu_1$, and the rib starts to slide. This situation is represented by dots and dashes in FIG. 9.

The lateral force $Fy_1$ generated by the tire is equal to the integral of the lateral stress in the contact area.

Figure 10:
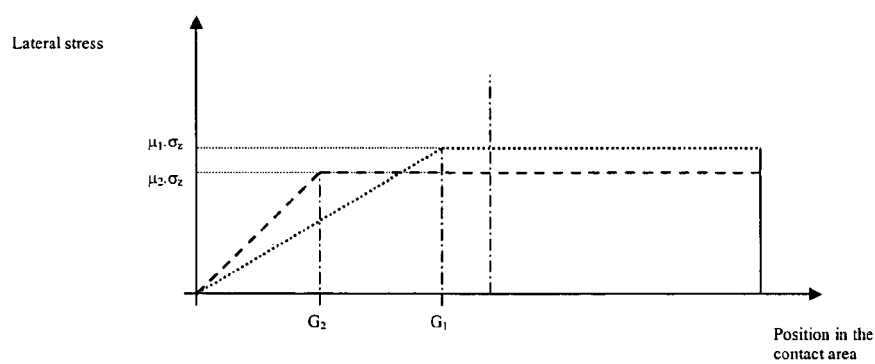
FIG. 10 illustrates the effect of the coefficient of friction on the distribution of the forces.

If the tire is rolling on a surface where the maximum friction potential $\mu_2$ is less than $\mu_1$, it is necessary to increase the drift angle so that the tire generates the same thrust force Fy. The slip region then starts at the point $G_2$ closer to the entry of the contact area. FIG. 10 allows the two situations to be compared.

Between these two configurations, the lateral forces are the same (same area under the curve) but the point of application of the force Fy has been displaced. The more the maximum friction potential decreases, that is to say the more the friction coefficient decreases, the more the point of application of the lateral force is displaced towards the entry of the contact area.

One consequence is that, for the same lateral force Fy, the self-alignment torque N has a different value. Between the two situations, the effects on the stresses associated with Fy are identical but those linked with N differ because of a displacement of the point of application of the force. These stress differences in the bead will be utilized in order to estimate the maximum friction coefficient.

Figure 11:
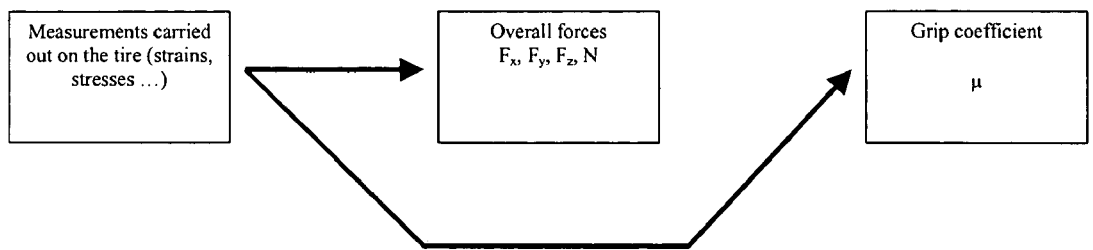
FIG. 11 is a block diagram of the estimation of μ from the deformation measurements.

A relationship has thus been established between the stresses in the bead of the tire, on the one hand, the overall forces applied to the tire, on the other hand, and the maximum friction coefficient. However, in order to have as much information as possible available for estimating the friction coefficient throughout the range of constraint, $\mu$ is estimated directly from the stress measurements carried out in the beads of the tire, without the intermediate step of estimating the forces from which $\mu$ is subsequently intended to be estimated (FIG. 11).

In particular, it is possible to use the measurement of the circumferential shear stress in the bead in order to estimate the maximum friction potential.

The measurement of the shear stress in the bead 1, on one side or on both sides of the tire, may be performed in any manner, using a device which is external to the tire or a device which is internal to the tire. By way of example, the use of one or more sensors 3 which are placed in an anchoring zone 2 of the carcass in the tire, and which are therefore carried along in rotation by the tire, will be described here for measuring the circumferential shear stress in the bead 1.

Figure 12:
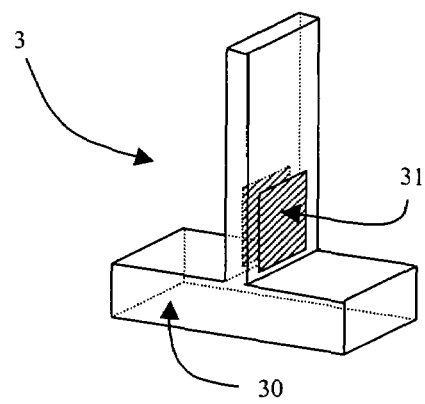
FIGS. 12, 13 and 14 illustrate a type of sensor which can be used for measuring the shear stresses, and its proposed installation in the bead.
Figure 13:
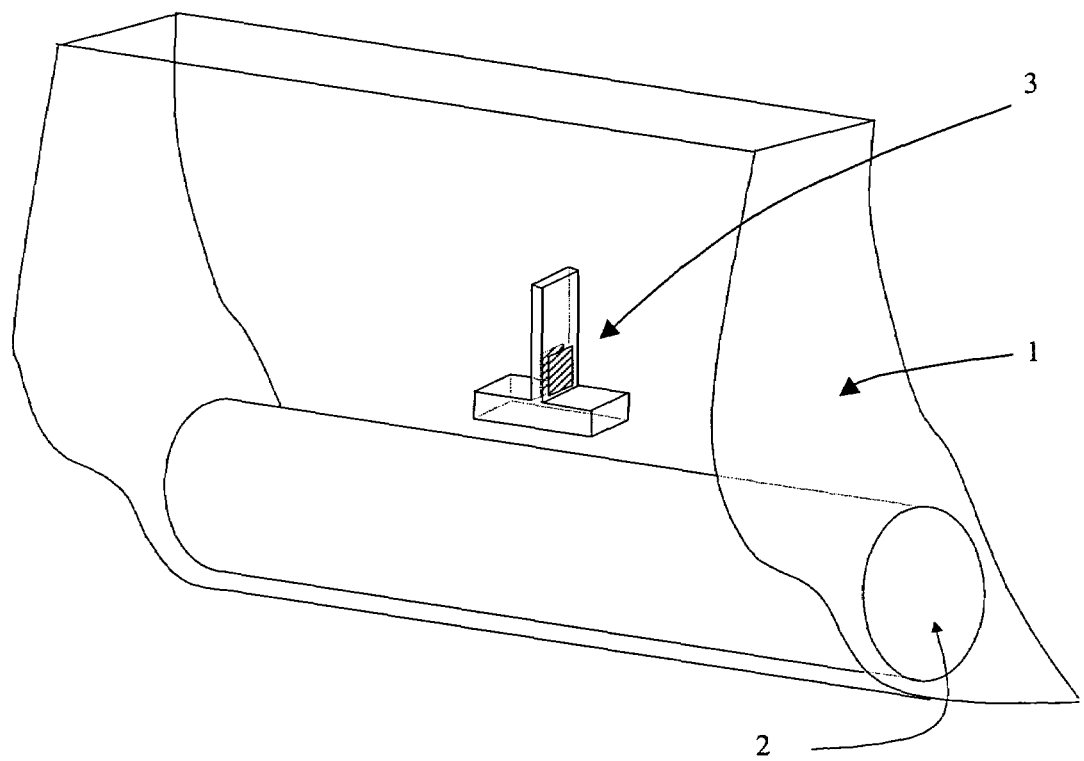
Figure 14:
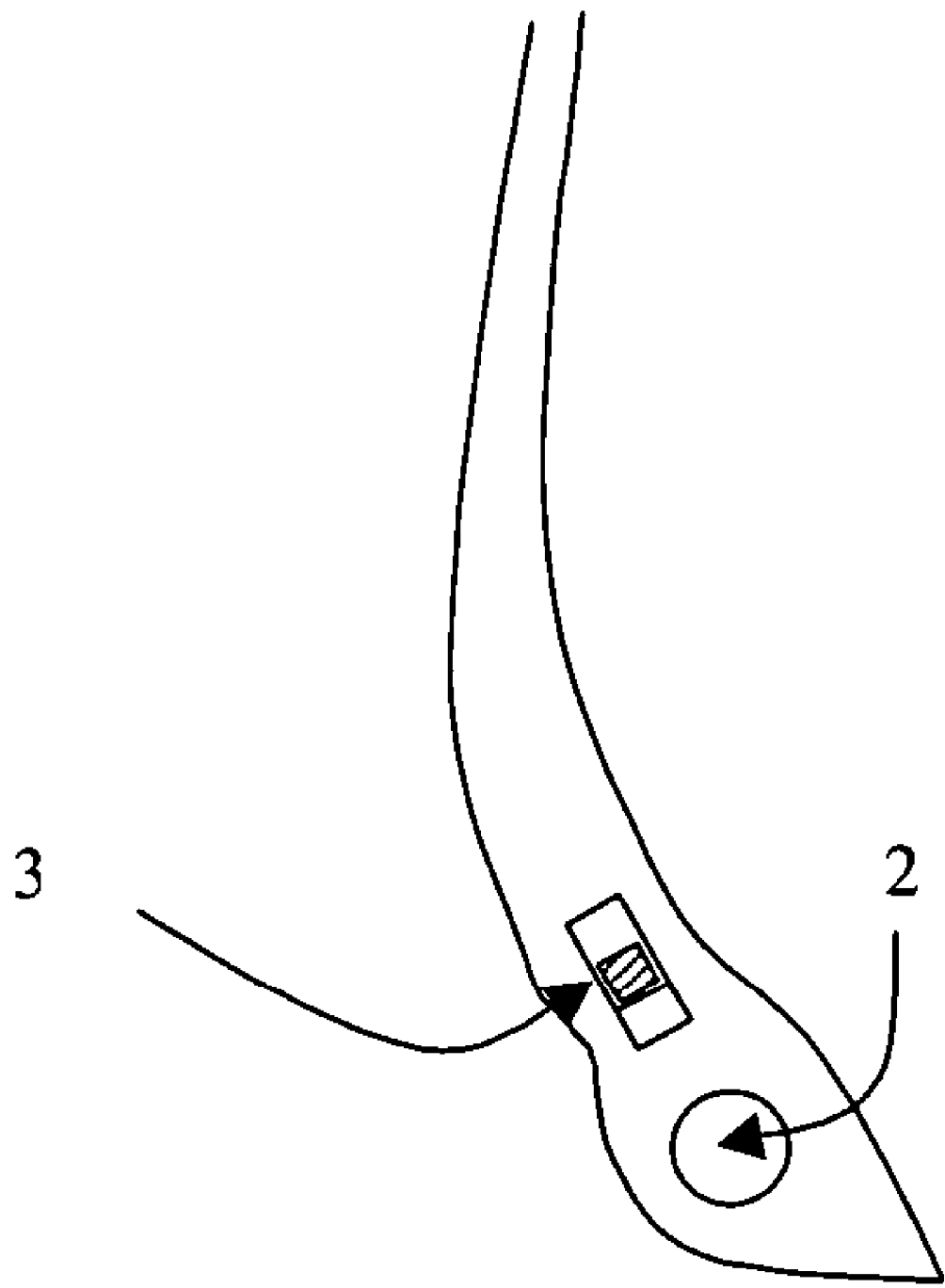

This sensor or these sensors 3, integrated in the tire and locally measuring the circumferential shear stress of the bead or beads, may employ any physical measurement principle. It may, for example, involve a test body 30 equipped with stress gauges 31, for example resistive gauges. Deformation of the test body leads to a modification of the resistance of the stress gauges 31 bonded to its surface (FIGS. 12, 13 and 14). Via a Wheatstone bridge, the two gauges 31 placed on either side of the test body 30 then provide a signal which is strongly linked with the shear stress. If the sensor 3 is an active sensor, it may be powered either by the vehicle, using wireless supply, or by a battery installed on the wheel or in the tire, or by any other means. There is also no limitation concerning transmission of the information to the vehicle, by radio or other means. The sensor 3 per se must be capable of delivering information continuously, or with a refresh frequency which is fast enough with respect to the period of rotation of the wheel.

This approach, using a sensor 3 integrated in the tire, has the advantage of making it possible to ascertain the shear stress in the bead on one side or on both sides, and at all the azimuths of the tire, since a sensor 3, when being carried along by the tire, explores all the azimuths during a rotation of the wheel.

An alternative way of increasing the precision or the robustness of the method consists in using a multi-dimensional measurement instead of a one-dimensional measurement. For example, and without implying any limitation, both a circumferential shear stress and a transverse shear stress may be used, the two quantities preferably, but without implying any limitation, being measured simultaneously by the same two-dimensional sensor at the same position.

The use of these two stresses makes it possible to provide a configuration, in which a single bead is equipped with sensor(s), which is as robust in terms of performance and as precise as a configuration in which both beads are equipped.

In this case, the inputs of the transfer function consist of an assortment of measurements of one or other or different types of stresses at various azimuths. Apart from this difference, exactly the same procedure is used for determining the transfer function. This approach can turn out to be very beneficial because, in terms of producing the final product, it may be much simpler and less expensive to equip only a single bead, even if the sensor itself is more expensive to manufacture.

In order to pick up the changes in the circumferential shear stress suitably, the measurements need to be carried out at expediently selected azimuths. In particular, and by way of a non-limiting example, the following cases may be indicated:

Measurement at three azimuths on both sidewalls. One azimuth selected at the entry of the contact area (for example between azimuths 100° and 150°), one measurement at 180° (center of the contact area) and one measurement at the exit of the contact area, at the azimuth which is symmetrical to the one used at the entry. This gives a total of six values of circumferential shear stresses, from which it is possible to estimate the maximum friction coefficient.

Measurement at seven azimuths on a single sidewall. The first three lie at the entry of the contact area, the fourth at 180° at the center of the contact area and the last three being symmetrical to the first three in relation to the center of the contact area.

Figure 15:
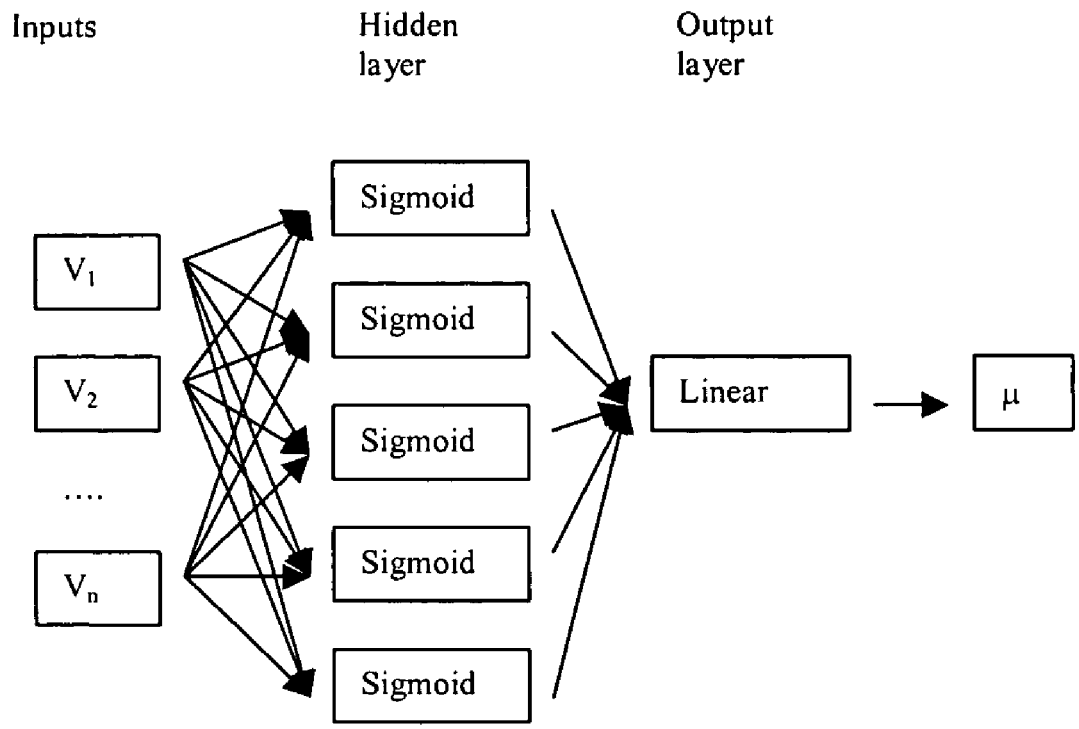
FIGS. 15 and 16 illustrate a neural-network type architecture which can be used for estimating μ with or without the pressure as an input.

In order to establish the transfer function between the shear stress measurements at a plurality of azimuths and the maximum friction coefficient, it is for example possible to use a neural network, of the perceptron type with a hidden layer, used as an approximator. FIG. 15 schematically shows this type of neural network. Any other mathematical function permitting this type of approximation may of course be used.

Figure 16:
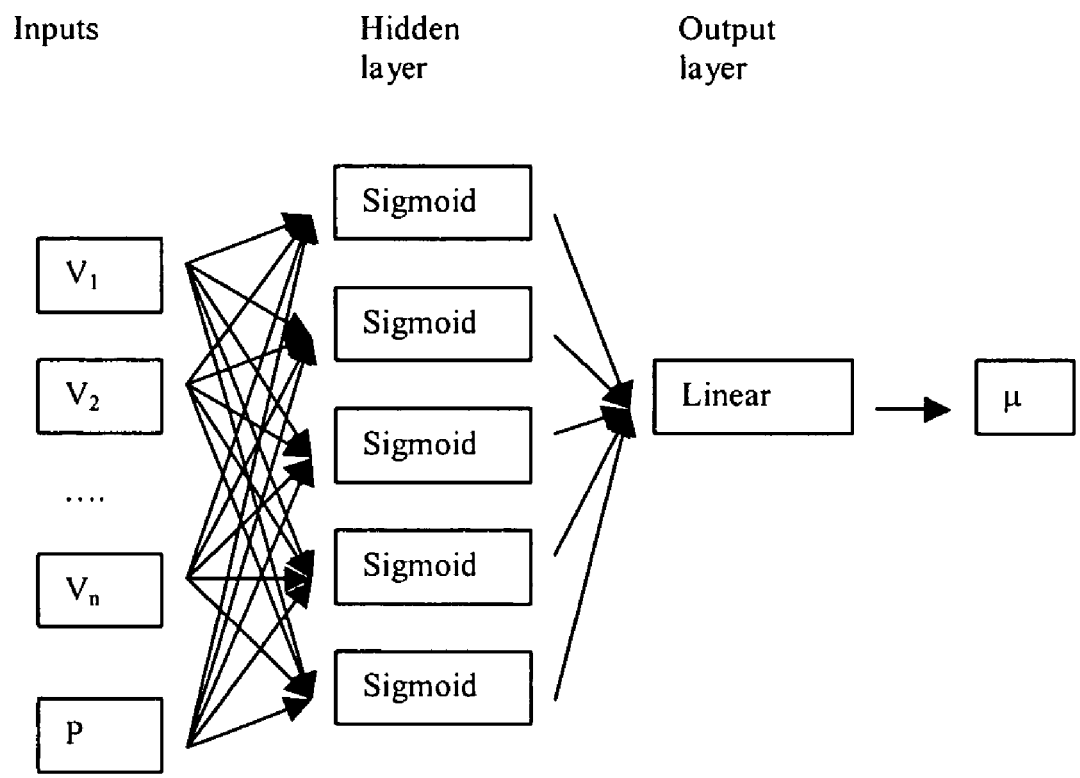

Numerous systems for measuring tire pressures are now available, and it is possible to make such measurements while driving. If such a system is available, the pressure may be used as an extra input of the transfer function, as indicated by FIG. 16. Of course, other quantities may be introduced at the input of the transfer function in order to improve its performance (for example, and without implying any limitation, the camber, the speed of the vehicle, etc.).

In the case when a neural network is used for forming the transfer function, the procedure adopted for constructing the function is as follows:

The first step consists in compiling a data base containing the values of the shear stresses at the selected azimuths (or any representative value), which will represent the inputs of the transfer function, and containing the values of $\mu$. It is possible to construct such a data base either with the aid of a measurement machine (the advantage is being able to constrain the tire with independent forces Fx, Fy, Fz and varying the friction coefficient in a well-controlled way) or on the vehicle by using, for example, a dynamometric wheel (for measuring the forces) and by driving over different ground surfaces.

If the future use of the system is to take place under conditions of variable camber and/or pressure, it is essential for the data base used in this step to contain camber angles and pressures representative of the future conditions of use.

The second step involves finding a transfer function with the aid of this data base, $\mu$ being the output of the transfer function. In the case when a neural network is used, this is the training phase.

The third step consists in checking that the transfer function which is obtained works correctly throughout the desired range, that is to say checking that it is generalisable.

In all cases, the proposed method for estimating the maximum friction coefficient requires that the tire be constrained by forces Fx, Fy, or both combined. In fact, it is absolutely necessary for there to be a slip region in the contact area, in order for the presented approach to be applied. This method ensures that an estimate of the friction limit can be obtained before it is reached. When the tire is being constrained very little, however, the estimate is imprecise or wrong (lack of slip in the contact area). For this reason, it is proposed to consider the percentage friction potential being used, which is defined in the following way:

$$p_u = \frac{\mu_{used}}{\mu} = \frac{\sqrt{F_x^2 + F_y^2}}{\mu \cdot F_z}$$

The approach proposed here consists in directly determining the percentage $p_u$ from the shear stress measurements. As for the determination of $\mu$, the procedure explained in the following paragraphs may be adopted.

The first step consists in compiling a data base containing the values of the shear stresses at the selected azimuths (or any representative value), which will represent the inputs of the transfer function, and containing $p_u$ (output of the transfer function) for a set of constraints. It is possible to construct such a data base either with the aid of a measurement machine (the advantage is being able to constrain the tire by independent forces Fx, Fy, Fz and varying the friction coefficient) or on the vehicle by using, for example, a dynamometric wheel (for measuring the forces) and by driving over different ground surfaces.

The second step involves finding a transfer function with the aid of this data base, $p_u$ being the output of the transfer function. In the case when a neural network is used, this is the training phase.

The third step consists in checking that the transfer function which is obtained works correctly throughout the desired range, that is to say checking that it is generalisable.

Figure 17:
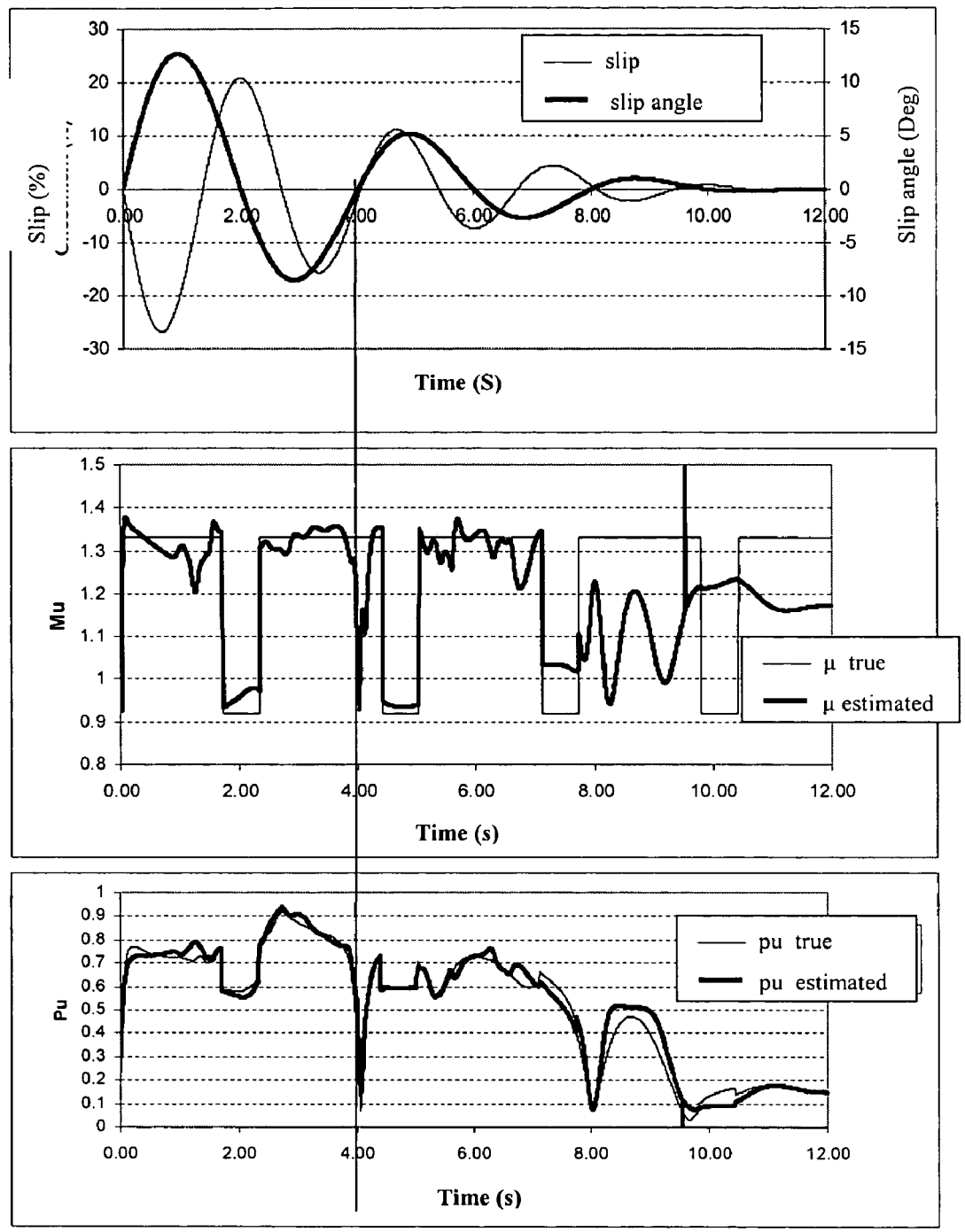
FIG. 17 gives the results of the estimation of μ and of the percentage of the friction potential used.

The proposed percentage has the benefit of being easier to estimate correctly as an absolute value regardless of the constraint, even if it is small, being applied to the wheel. It is obtained directly, for example using a neural network, by applying the approach presented for the estimation of $\mu$. FIG. 17 presents an example of reconstructing the maximum friction coefficient and the percentage potential used. The driving or braking torque (slip associated with Fx) and the transverse force (drift angle associated with Fy) vary as a function of time as well as the ground surface on which the vehicle is driving. The load Fz is imposed. When the constraint of the tire is small (Fx and Fy both small at the same time), at around 4 s, the quality of the estimate of the maximum friction coefficient drops. The estimate of percentage potential used, for its part, remains quite correct.

In the context of use by a system fitted on-board a vehicle (a system such as ESP or ABS), it is beneficial to have available a quantity defined throughout the range of use. It is, for example, conceivable to use the percentage friction potential used (pu) in order to refine the control mechanisms of ABS or ESP systems.

What is claimed is:

1. A method of determining a friction coefficient $\mu$ in a contact area of a tire on a road, comprising:
   selecting a plurality of fixed points within at least one bead of the tire, wherein the plurality of fixed points lie at different azimuths along at least one circle within the at least one bead of the tire;
   measuring a shear stress value at each of the plurality of fixed points while the tire is rolling on the road; and
   processing the measured shear stress values to determine the friction coefficient $\mu$.

2. The method according to claim 1, wherein the friction coefficient $\mu$ is derived from at least 5 measurements of shear stress carried out in the at least one bead of the tire.

3. The method according to claim 1 or 2, wherein the measurement of the shear stress values is carried out by at least one sensor integrated in the at least one bead of the tire, and signals transmitted by the sensor are processed in order to acquire the shear stress values at the plurality of azimuths corresponding to the fixed points.

4. The method according to claim 1 or 2, wherein the measurement of the shear stress values is carried out by as many sensors as there are fixed points, the sensors being external to the tire, and each sensor being located at a fixed position relative to a body of a vehicle utilizing the tire.

5. The method according to claim 1, wherein the measurements are carried out at at least three azimuths on each of two beads of the tire: (a) at an azimuth at an entry point of the contact area, (b) at an azimuth of 180°, and (c) at an azimuth at an exit point of the contact area, the entry and exit points being arranged symmetrically with respect to the contact area.

6. The method according to claim 1, wherein the measurements are carried out at at least seven azimuths on a single bead of the tire, so that: (a) three of the azimuths lie at an entry point of the contact area, (b) one azimuth lies at 180° at a center of the contact area, and (c) three azimuths lie at an exit point of the contact area, the entry and exit points being arranged symmetrically with respect to the contact area.

7. The method according to one of claims 1, 2, 5, or 6, further comprising establishing a relationship between the measured shear stress values and a maximum friction coefficient by:
   compiling a data base containing the measured shear stress values and the associated values of $\mu$, all of the shear stress values being acquired experimentally; and
   determining a transfer function using the data base, wherein $\mu$ is an output of the transfer function.

8. The method according to claim 7, wherein a neural network of the perceptron type, with a hidden layer, is used as an approximator to determine the transfer function.

9. The method according to one of claims 1, 2, 5, or 6, wherein the shear stress values are estimated by measuring flexure of a test body inserted into the at least one bead of the tire.

10. The method according to one of claims 1, 2, 5, or 6, wherein the shear stress values are estimated by measuring flexure of a test body using strain gauges.

11. The method according to one of claims 1, 2, 5, or 6, further comprising determining a percentage friction potential, defined by $$p_u = \frac{\mu_{used}}{\mu} = \frac{\sqrt{F_x^2 + F_y^2}}{\mu \cdot F_z},$$

the percentage friction potential being determined by:
   compiling a data base containing the measured shear stress values, for a set of constraints of the tire;
   determining a transfer function using the data base, wherein $P_\mu$ is an output of the transfer function and the measured shear stress values are inputs of the transfer function; and
   checking that the transfer function is valid throughout a desired range of constraints.

* * * * *

UNITED STATES PATENT AND TRADEMARK OFFICE
CERTIFICATE OF CORRECTION

PATENT NO.        : 7,398,146 B2
APPLICATION NO.   : 11/015353
DATED             : July 8, 2008
INVENTOR(S)       : David Bertrand Page 1 of 1

It is certified that error appears in the above-identified patent and that said Letters Patent is hereby corrected as shown below:

ON THE TITLE PAGE ITEM (73):

Assignee, "Michelin Recherche Et Technique S.A. (CH)" should read --Michelin Recherche et Technique S.A., Granges-Paccot (CH)--.

SHEET 3:

F3a, "Azimut (Deg)" should read --Azimuth (Deg)--; and
F3b, "Azimut (Deg)" should read --Azimuth (Deg)--.

SHEET 4:

F4a, "Azimut (Deg)" should read --Azimuth (Deg)--; and
F4b, "Azimut (Deg)" should read --Azimuth (Deg)--.

COLUMN 10:

Line 19, "wherein $P_u$" should read --wherein $p_u$--.

Signed and Sealed this

Seventeenth Day of February, 2009

JOHN DOLL
*Acting Director of the United States Patent and Trademark Office*